United States Patent

Nanko

[11] Patent Number: 5,772,574
[45] Date of Patent: Jun. 30, 1998

[54] DEVICE FOR MEDICAL RADIATION THERAPY

[75] Inventor: Norbert Nanko, Freiburg, Germany

[73] Assignee: B.V. Optische Industrie "De Oude Delft", Delft, Netherlands

[21] Appl. No.: 663,214
[22] PCT Filed: Dec. 9, 1994
[86] PCT No.: PCT/EP94/04106
   § 371 Date: Aug. 29, 1996
   § 102(e) Date: Aug. 29, 1996
[87] PCT Pub. No.: WO95/16489
   PCT Pub. Date: Jun. 22, 1995

[30] Foreign Application Priority Data

Dec. 14, 1993 [DE] Germany .......................... 43 42 589.5

[51] Int. Cl.⁶ ...................................................... A61N 5/00
[52] U.S. Cl. .................................................................. 600/1
[58] Field of Search ............................................. 600/1–9

[56] References Cited

U.S. PATENT DOCUMENTS 2,829,636  4/1958  Henschke .
4,963,128  10/1990  Daniel et al. .
5,030,195  7/1991  Nardi .

FOREIGN PATENT DOCUMENTS 390 884 B    7/1990   Australia .
0 292 630 A1 11/1988  European Pat. Off. .
283 071 A5   10/1990  Germany .

Primary Examiner—John P. Lacyk
Attorney, Agent, or Firm—Panitch Schwarze Jacobs & Nadel, P.C.

[57] ABSTRACT

A device for medical radiation therapy uses in the treatment area a deformable carrier mat (1) which can be placed on the patient. This carrier mat (1) has prefabricated mounting channels (7) running inside its mat plane to accommodate or to insert the guide sleeves (2), in which an essentially point-shaped radiation source (5) can be displaced and positioned. The carrier mat (1) is made of one piece from silicone or a silicone-like material which can be autoclaved. The carrier mat (1) is constructed from a plurality of spheres (9) or rounded, sphere-like, ball-shaped bodies (9a) which are provided adjacent to each other and are connected with each other by means of collar sections (8), while the mounting channels (7) run through the spheres (9) and/or the collar sections (8). Due to this even in the case of a minimum thickness of the carrier mat (1) a particularly good mobility and shape adaptability is present.

28 Claims, 7 Drawing Sheets

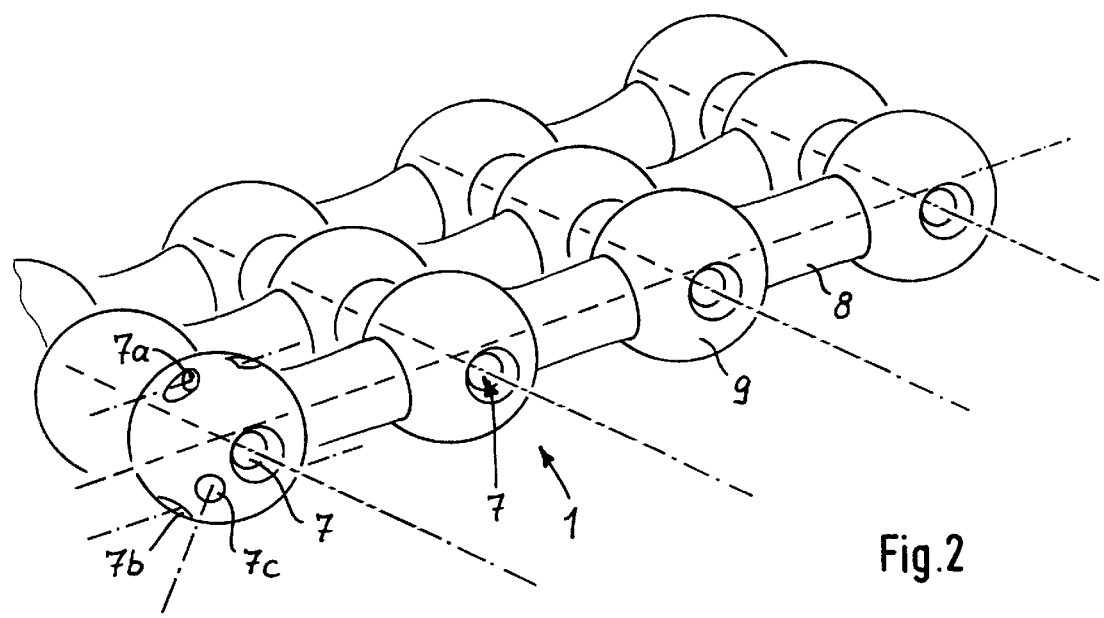
Fig. 2
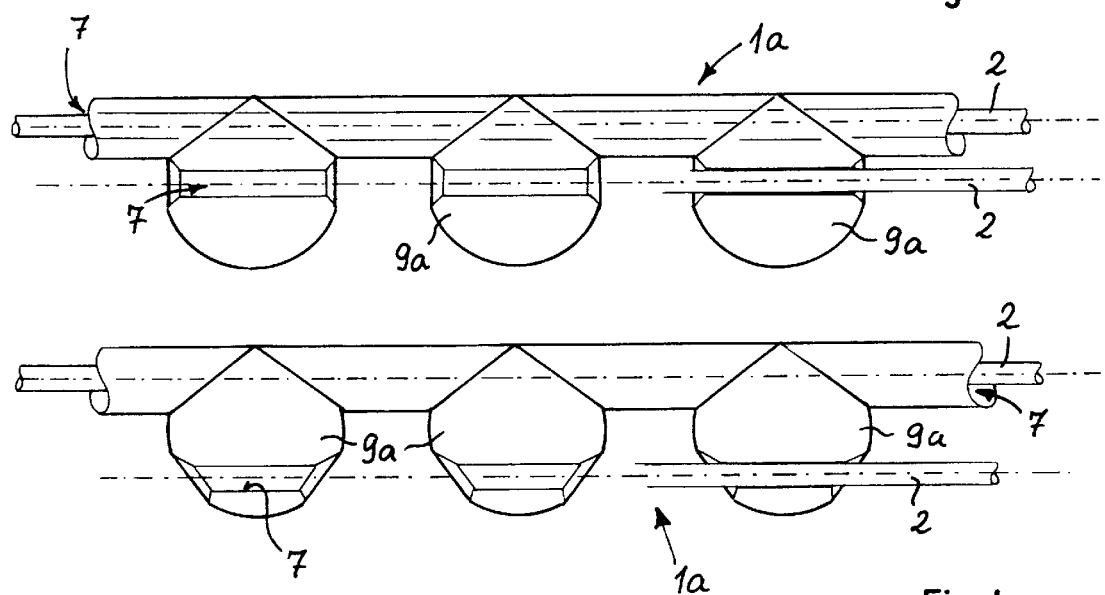
Fig. 3
Fig. 4

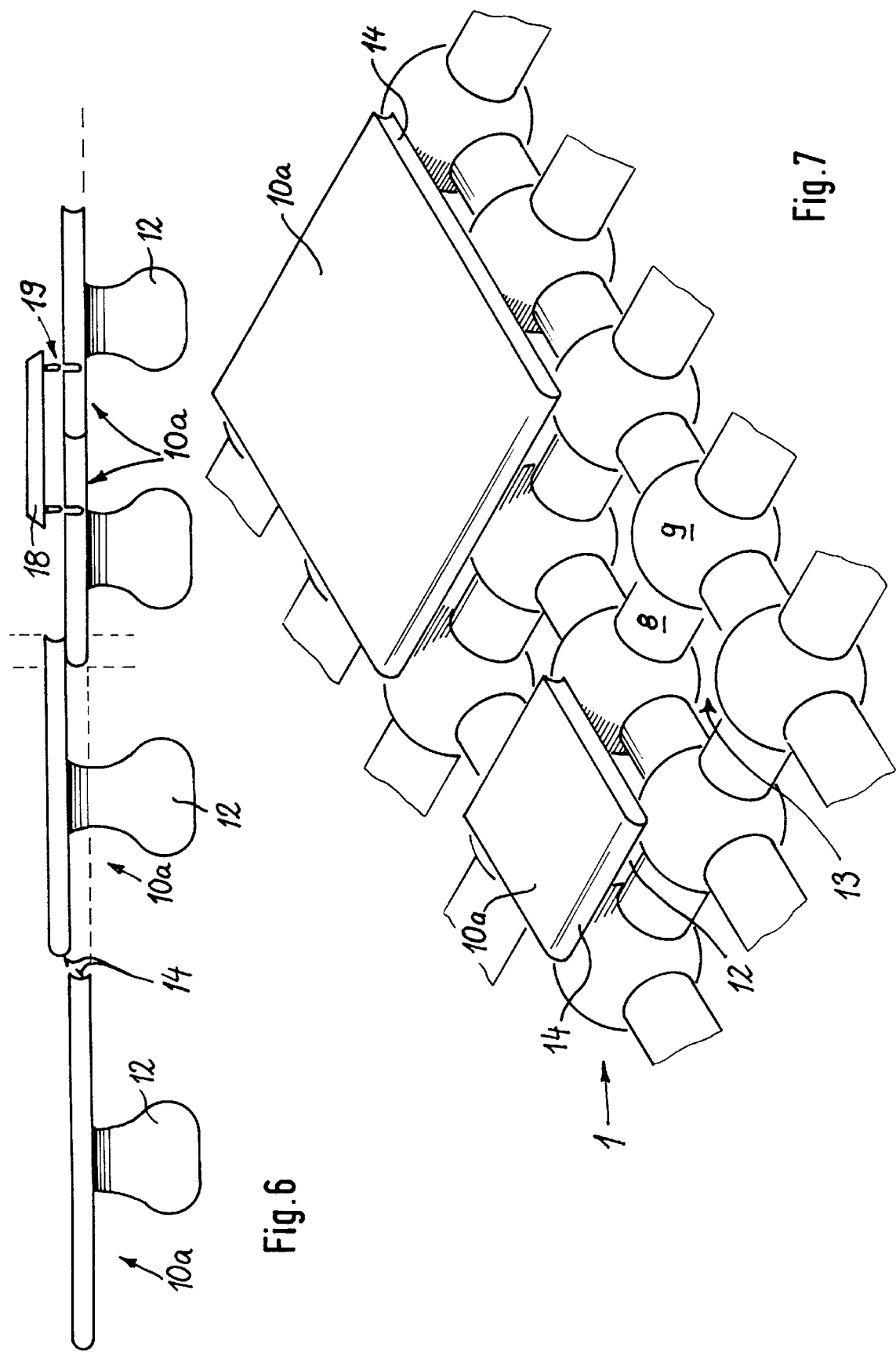

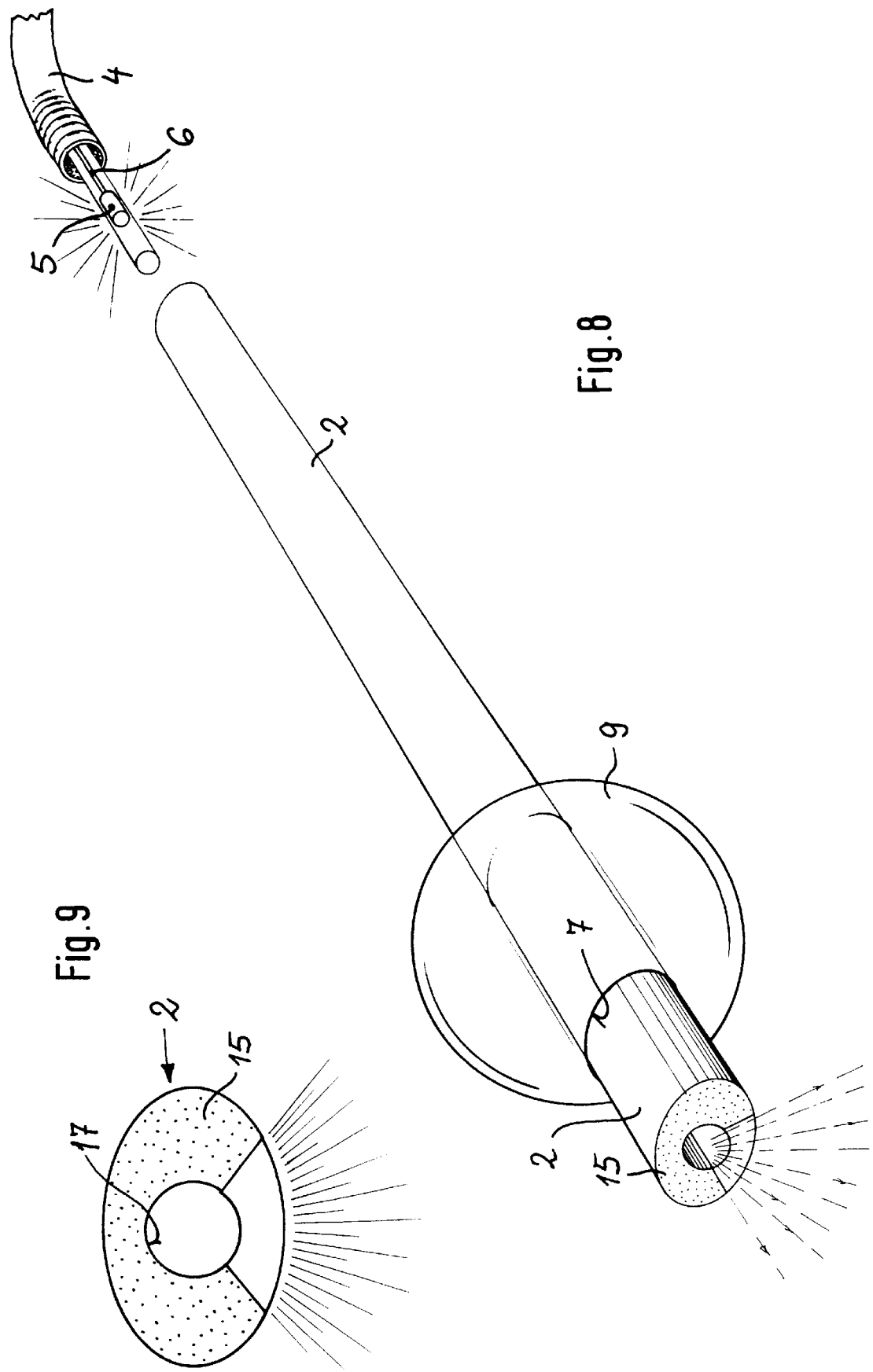

DEVICE FOR MEDICAL RADIATION THERAPY

FIELD OF THE INVENTION

The invention concerns a device for medical radiation therapy with a deformable carrier mat for guide sleeves which can be applied in the treatment area of patients, in which mat a radiation source which is essentially point-shaped can be displaced and positioned, wherein the carrier mat has prefabricated mounting channels running within its mat plane to accommodate the guide sleeves or the like.

BACKGROUND OF THE INVENTION

In radiation therapy the so called afterloading technique is already known, wherein a tube-shaped applicator, constructed as a guide sleeve, is first brought to a desired position at the position to be treated. Following this a radioactive preparation, as the radiation source, is pushed by remote control from a radiation protective container to the treatment position in the applicator through a hollow sonde which is coupled with the applicator.

As support for several guide sleeves or applicators, moulages made of a pliable deformable material, e.g. plasticine, foam rubber or the like are used, into which the needle-shaped guide sleeves are inserted. To the outside ends of the guide sleeves hollow probes can be joined, which are connected to the afterloading device and through which the radiation sources situated in the radiation protection container can be pushed one after the other into the individual guide sleeves (applicators).

For a targeted therapy it is necessary to position the guide sleeve accurately within the carrier mat (moulage). At the same time it should be remembered that the radiation intensity does not decrease linearly with the distance to the radiation source, but, depending on the secondary radiation, there is a maximum intensity at a certain distance from the radiation source.

Thus for the calculation of the radiation dosage the position of the moulage itself relative to the treatment area on the one hand and the position of the guide sleeves within the carrier mat on the other, are of importance.

When inserting the guide sleeves made of plastic material into the carrier mat the problem arises that a straight course of the guide sleeves and an accurate maintenance of the constant distance to the surface of the carrier mat and to the adjacent guide sleeves cannot be realised in practice.

SUMMARY OF THE INVENTION

To keep a lateral deflection of the guide sleeves in check when inserting them into the carrier mat, steel mandrels are pushed into the guide sleeves for the insertion operation to achieve a somewhat greater rigidity. Despite this during manual insertion, an accurate maintenance of the position of the guide sleeves is not feasible within the required limits.

A further problem arises due to the fact that the guide sleeves should to be as short as possible because the inserting operation becomes more difficult as the length of the guide sleeve increases and for this reason they are essentially determined by the size of the carrier mat. The connections for the hollow probes which lead to the afterloading device are thus in the vicinity of the carrier mat and, when treating the inside of the body, consequently inconveniently in an area where the contact positions with the body fluids, blood and the like may come into contact.

From EP 292 630 A1 a device for medical radiation therapy is already known, which has prefabricated mounting channels situated within its mat plane for the guide sleeves, so that accordingly an accurate positioning for a radiation source is feasible. The carrier mats used in this case are conceived as once-only products and are made of absorbing material. They are also very thin.

As it has been already mentioned, it needs to be considered that the radiation intensity does not decrease linearly with the distance, but that there is a maximum intensity at a very definite distance from the radiation source.

A typical (minimum) distance of the radiation source from the treatment place is approx. 5 mm, so that the carrier mat serving the purpose of guiding as well as spacing must have a corresponding thickness, e.g. approx. 10 mm. However, a 10 mm thick mat cannot be well shaped or not satisfactorily anyway, so that the distance to the radiated area determined by the mat itself cannot be always adhered to.

The object of this invention is to produce a device for radiation therapy of the type mentioned in the introduction, wherein an accurate calculation of the radiation dosage to be administered can be carried out in practice with good accuracy. For this purpose the carrier mat should be relatively thick even in those areas which have relatively strong curvatures despite the prerequisites of the radiation physics. Finally, the carrier mat should be able to be used again.

To achieve this objective the invention proposes that the carrier mat is made in one piece from silicone or a silicone-like material which can be autoclaved, that the carrier mat is constructed from a plurality of spheres or rounded, sphere-like, ball-shaped bodies arranged next to each other and joined by collar sections and that the mounting channels run through the spheres and the collar sections.

The deformability of the carrier mat is considerably improved by this and, in addition, due to this only point supports on the tissue to be treated are provided, so that particularly when treating inside of the body an undesirable adhesion is prevented.

By virtue of the material used the carrier mat is highly flexible on the one hand end there is the possibility on the other to sterilise the carrier mat after use in an autoclave. Thus the carrier mat is reusable and can be used cost-effectively.

The rounded or spherical shape of the individual elements provided for the particularly good deformability of the carrier mat due to the smooth, niche-free surfaces contributes to the simplicity of sterilisation of the carrier mat. Finally, the carrier mat can be manufactured relatively simply by, for example, a casting process.

Due to the prefabricated mounting channels running inside of the plane of the mat of the carrier mat, to accommodate or insert the guide sleeves or the like, advantageously there is the possibility to push in the guide sleeves problem-free to those positions in the carrier mat into an already existing mounting channel which is accurately determined with regard its position and its course. Accordingly, the pushed in guide sleeve is also accurately laid inside of the carrier mat, so that due to this position an accurate radiation dosage can be calculated. The use of a mandrel as auxiliary tool for the introduction of the guide sleeves is no longer necessary. The length of the guide sleeves, is no longer relevant either, so that their length can be dimensioned so that their external connecting ends for the hollow probe(s) are situated at an easily accessible place.

According to an advantageous development of the invention the mounting channels are provided in a specified grid and the mounting channels are provided preferably parallel next to each other with the same particular lateral distances from each other.

When fitting the mounting channels situated in the carrier mat with guide sleeves, in case of such a grid pattern one has an adequate choice for an individually suitable fitting pattern, so that a universal carrier mat can be used for most applications.

A further development of the invention provides that at least a portion of the mounting channels is provided offset relative to the central plane running parallel to the flat sides of the carrier mat.

If, for example, all mounting channels are offset relative to the central plane, i.e. are nearer to one flat side than the opposing flat side, then, by turning over the carrier mat, different distances can be set to the tissue to be treated. In the case when the mounting channels are provided in a zigzag shaped cross-section, especially on both sides of the central plane, different radiation distances can be set in the course of the carrier mat.

A development of the invention provides that the carrier mat has recesses preferably between the mounting channels or the spheres or the like. This will improve the deformability and adaptability of the carrier mat and its use under narrow conditions and when the mat is placed on strongly undulating areas, is also feasible.

A preferred embodiment of the invention provides that the spheres on those sides which face each other in the region of the connecting positions with the collar sections are flattened by half the length of the collar section and that the centre distance of adjacent spheres corresponds to their diameter.

By virtue of this measure the lateral grid distance of adjacent spheres or the mounting channels situated in them can correspond exactly to the diameter of the spheres, so that in an advantageous manner the same dimensions can be assumed in all three coordinate directions.

If necessary, in case of a suitable choice of material for the carrier mat the mounting channels themselves can be constructed as guides for the radiation source or for the hollow probes connected to the afterload device. In this case no separate guide sleeves are required. In the case of this embodiment at one end of the guide channels and mounting channels couplings may be provided for the hollow sondes.

There is the further possibility to provide the carrier mat with guide sleeves inserted during the manufacture. In case of this construction a subsequent fitting with guide sleeves is not necessary.

A development of the invention provides that in case of the carrier mat and/or guide sleeves radiation shield elements are provided on their rear side to suppress an undesirable radiation at the rear. An undesirable radiation at the rear can be prevented or at least reduced by these radiation shield elements.

At the same time it is provided in a preferred manner that on the shield elements supports are provided to join to the carrier mat, which supports are designed preferably to engage the recesses of the carrier mat, particularly in the form of a mushroom. If necessary, these shields can be fitted particularly where the radiation source is moved along. By means of these supports a rapid assembly and dismantling or removal of the shield elements is possible.

It is advantageous if the shield elements are constructed in the shape of a strip or sphere and if they extend at least over the extent of a sphere and, if appropriate, the collar sections adjoining it. Due to this the good adaptability of the carrier mat to suit a shape will be hardly affected.

If necessary, the guide sleeves can have at least partial radiation shields, which overlap a section of the circumference of the guide sleeve. In this manner a shielding is present already close to the radiation, resulting in a particularly effective shielding when combined, if necessary, with a shielding on the carrier mat, making otherwise necessary separate shieldings mostly superfluous.

BRIEF DESCRIPTION OF THE DRAWINGS

Additional developments of the invention are specified in the further sub-claims. In the following the invention with its essential details is explained in detail based on the drawings. Shown is in:

DETAILED DESCRIPTION OF PREFERRED EMBODIMENTS

Figure 1:
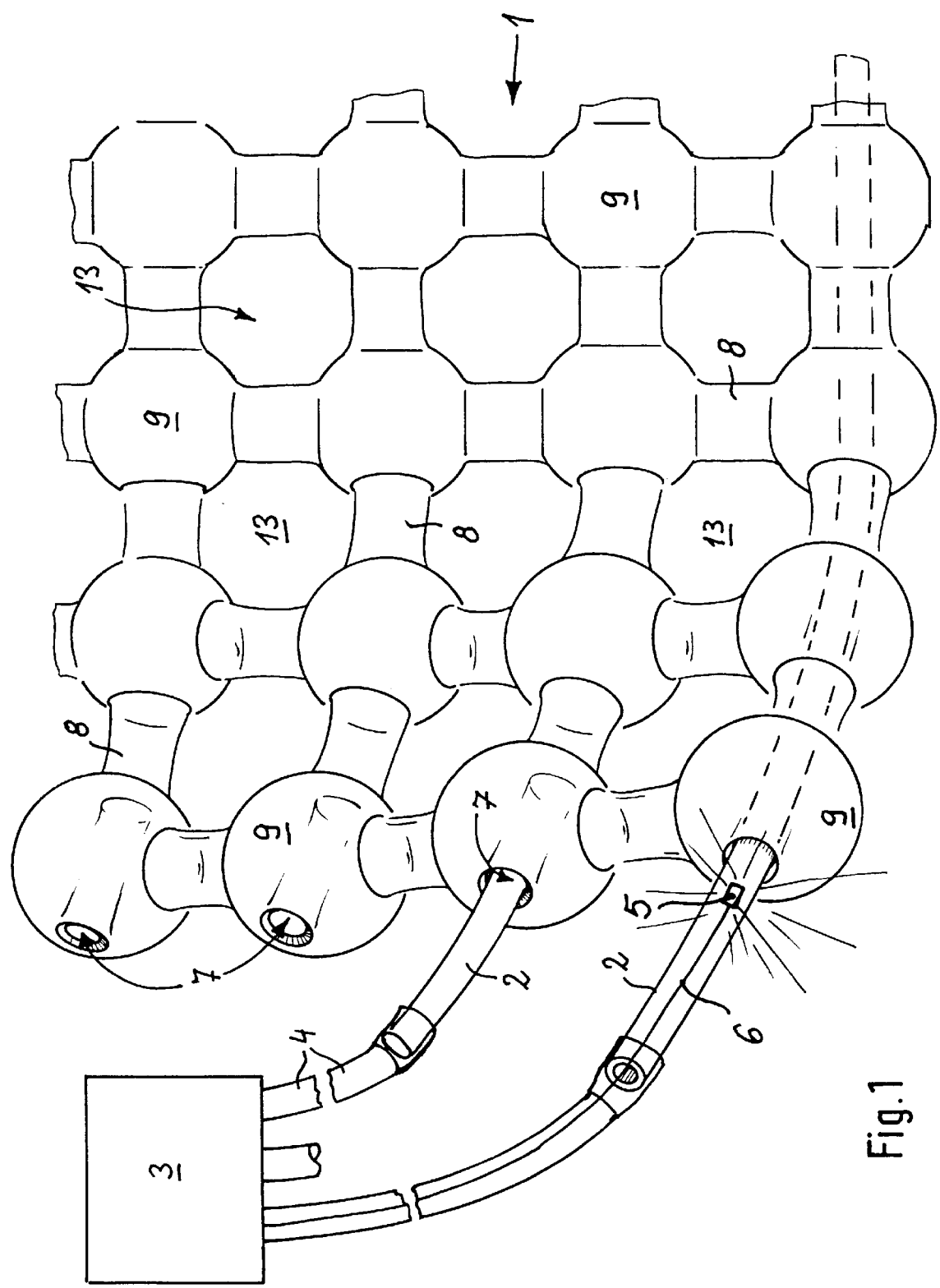
FIG. 1 a perspective view of a partial section of a carrier mat and the schematically indicated afterloading device, FIG. 2 a partial section of a carrier mat with different mounting channels in it, FIGS. 3 and 4 small side views of carrier mats with various mounting channels, FIG. 5 a perspective partial view of a carrier mat with radiation shield elements, FIG. 6 a side view of several radiation shield elements, FIG. 7 a partial view of a carrier mat with tile-shaped radiation shield elements, FIGS. 8 and 9 guide sleeves with radiation shields provided on the circumference, FIGS. 10 to 13 side views of carrier mats with mounting channels having different sections, and FIG. 14 top view of a partial section of a carrier mat with identification code of the individual rows of mounting channels.

A carrier mat 1 shown in FIG. 1 serves in the embodiment to accommodate guide sleeves 2. The purpose of the carrier mat is medical radiation therapy and it is positioned in the area of treatment at the position to be treated. An essentially point-shaped radiation source, consisting of a radio active preparation, is introduced in succession into the guide sleeves 2 and positioned in these guide sleeves for accurately predetermined time intervals. The radiation source is then pulled out from one guide sleeve and introduced into another guide sleeve of the carrier mat and positioned there.

The guide sleeves or applicators, into which the radiation preparation are to be introduced, can be joined to a hollow probe 4 leading to the afterloading device 3. The afterloading device 3 contains a radiation protection container for the radiation source 5 into which it can be pulled back by a transport wire 6 after the respective treatment. The afterloading device 3 can be programmed so that the radiation source is introduced in succession into the respective guide sleeves 2 and is also positioned in the area of the carrier mat 1 at certain places.

The carrier mat 1 is fitted before a treatment with guide sleeves 2 corresponding to the size and position of the treatment field. For this purpose the carrier mats 1 are provided with mounting channels 7 which are provided next to each other in a grid pattern. The guide sleeves 2 are introduced directly into these. Special aid elements, like, for example, steel mandrels, which have been necessary so far for the insertion of the needle-shaped guide sleeves into a carrier mat not having mounting channels 7, are no longer required.

The guide sleeves 2 are guided accurately in a specified manner by the mounting channels 7 contained already in the carrier mat 1, so that a precise calculation of the radiation dosage or the respective dwell time of the radiation source 5 at specified places is also possible.

An accurately specified distance of the radiation source from the surface of the area to be treated is determined by the carrier mat 1, which is described also as moulage.

The carrier mat 1 can be, for example, approx. 10 mm thick, to achieve a homogeneous radiation field and a homogeneous radiation dosage when using a conventional radiator.

To enable the variation of the position of the guide sleeves 2 introduced into the carrier mat 1 and consequently also the position of the subsequently introduced radiation source 5, the carrier mat 1 can have also mounting channels 7 provided outside of its central plane. In FIG. 1 the mounting channels 7 are provided approximately in the central plane and FIG. 2 shows an embodiment of a carrier mat wherein additional non-centrally situated mounting channels 7a, 7b are provided. These mounting channels are shown in FIG. 2 only on one of the spherical elements from which the carrier mat 1 is constructed. They are, however, continued in the direction of alignment in the respective adjacent spherical bodies, as this can be seen in FIGS. 3 and 4.

There is the further possibility to provide transversely situated mounting channels 7c (FIG. 2).

The carrier mat 11[sic] can be made of an easily deformable, adaptable, plastic material which is essentially a flat body. To provide a particularly easy movement and deformability for the carrier mat even if it is slightly thicker, e.g. 10 mm or more, it is envisaged that the carrier mat comprises a plurality of spheres 9 which are provided next to each other and are joined with each other via collar sections or similar rounded bodies 9a. The embodiment according to FIGS. 1 and 2, for example, are preferred. In this case the mounting channels 7 run both through the spheres 9 and the collar sections 8. Moreover, FIG. 2 shows the further mounting channels 7a and 7c, which run through the spheres only. However, since in a carrier mat 1 prepared for the treatment the guide sleeves 2 are inserted, a continuous guiding is available for the radiation source 5 inside the guide sleeves 2 which are inserted into the mounting channels 7a or 7b or 7c. The carrier mat 1 according to FIGS. 1 and 2 is constructed symmetrically relative to the central plane and consequently has a very good deformability and mobility in both directions.

An asymmetrical construction of the carrier mat 1a is, however, also possible according to FIGS. 3 or 4. In these cases the joining collar sections 8 are not in the centre of the body 9a but offset towards one surface.

The diameter of the spheres 9 or of the rounded bodies 9a, the cross-section of the collar sections 8 as well as the distances between the spheres or the collar sections may be varied to suit the requirements and is adjusted to suit particularly the required distance conditions and the mobility of the carrier mat.

Figure 5:
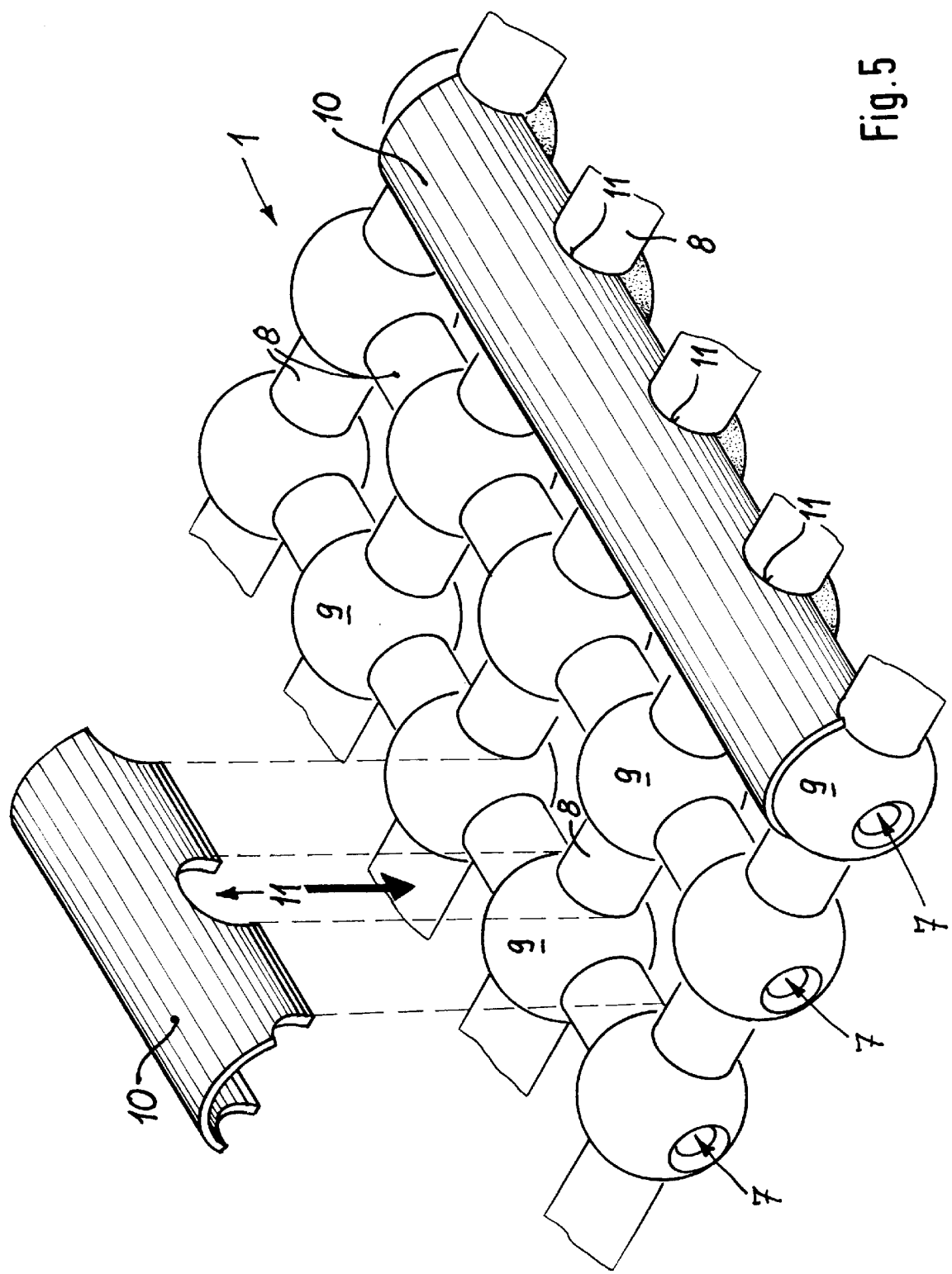

To prevent an all-round radiation from the radiation source 5 and in particular the radiation and possible damages to the tissues situated outside of the treatment area, different steps can be taken for the shielding, as this is shown particularly in FIGS. 5 to 9. FIG. 5 shows approximately shell-shaped radiation shield elements 10, which can be fitted along on the mounting channels 7 situated in the carrier mat 1. To join these shield elements 10 with the carrier mat 1, locking recesses 11 are provided on the shield elements, which recesses engage on both sides of a sphere 9 the collar sections 8. The inside diameter of the locking recesses 11 corresponds approximately to the diameter of the collar section 8, whereby the locking recesses extend approximately in a semi-circular shape, so that the exposed bottom edges overlap the collar sections 8 in a locking mariner. Due to this the shield elements 10 can be clipped into the respective envisaged positions. In a preferred manner the shielding is effected by a plurality of relatively short shield elements 10, thus retaining the mobility of the carrier mat 1 to the greatest extent. These shield elements extend therefore preferably only over the region of one sphere 9 and, if applicable, the adjoining collar sections 8. For those applications, where the carrier mat 11[sic] is arranged to be flat, or is deformed in one plane only, longer shield elements 10 can be also used.

FIGS. 6 and 7 show approximately tile-shaped shield elements 10a, which have mushroom-like locking elements 12 for clipping into the recesses 13 of the carrier mat 1, 1a. The shield elements 10a, as well as the shield elements 10, may have on their edges engagement sections 14, so that adjacent shield elements engage each other at the edges and thus a transition 10 with a high degree of radiation capacity is achieved (FIG. 6). There is, however, the possibility to construct the shield elements in such a manner that a roof tile-like overlapping is formed, as this is also illustrated in FIG. 6. To cover the separating regions between adjacent shield elements 10a, shielding cover elements 18 (FIG. 6) may be provided. These can be attached to the shield elements 10a by, for example, plug-in locking connectors 19.

The tile-like shield elements 10a according to FIGS. 6 and 7 may also be of different sizes. In the case of small shield elements a single locking element may be provided centrally, whereas in the case of large-surface shield elements more than one locking element 12 may be provided to assure a reliable holding.

Figure 10:
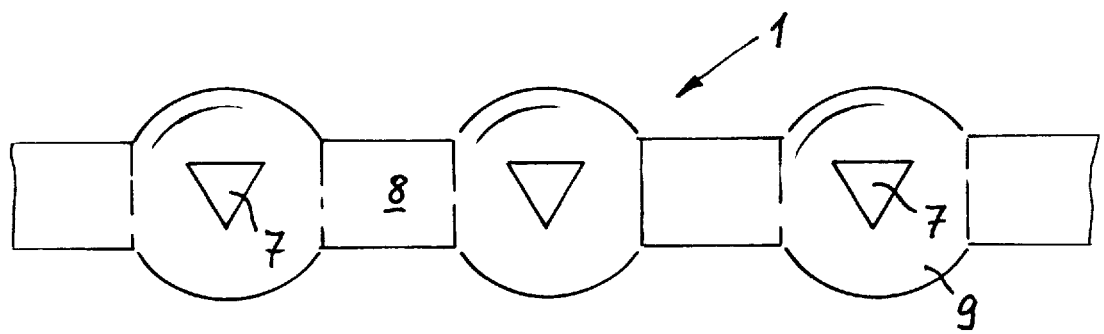
Figure 11:
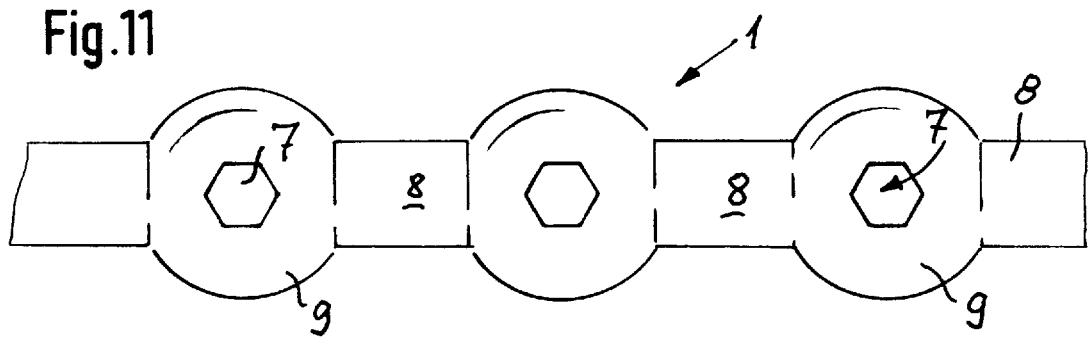
Figure 12:
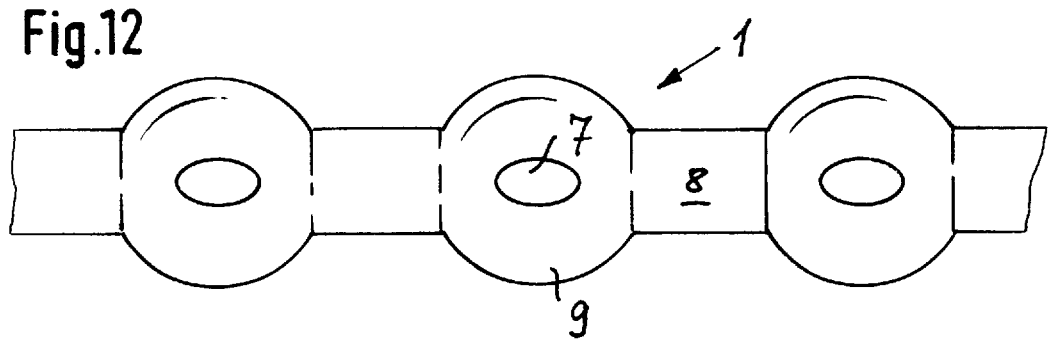
Figure 13:
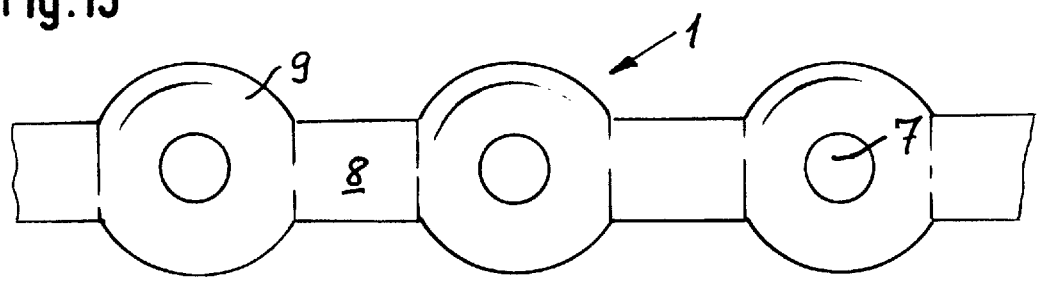

FIGS. 8 and 9 show further possibilities of radiation shielding measures. In this case the shielding 15 is carried out directly by the guide sleeves 2. In the case of this embodiment part of the circumference of the wall of the guide sleeve 2 which bounds the inside hole 17 is made of a shielding material, wherein the size of the peripheral section determines also the possible angle of radiation on the opposite side. For the fixing of the position of such a shielding guide sleeve within the mounting channel 7 the guide sleeves 2 and the mounting channels 7 in the carrier mat 1 have longitudinal sections which fit into each other. In the embodiment according to FIGS. 8 and 9 and also FIG. 12 the cross section envisaged has an oval cross-section. However, other cross-sections may be also provided, as this is shown in FIGS. 10 and 11. Moreover, asymmetrical sections can be used also in the circumferential direction, due to which the insertion of the guide sleeves 2 can be carried out only in one particular position.

The individual shielding measures, like they are shown in FIGS. 8 and 9, or in FIGS. 6 and 7, or in FIG. 5, may be also used in combination with each other. It should be also mentioned that for the shielding of the radiation source 5 guided in the guide sleeves 2, push-on longitudinally slotted shield sleeves could also be provided. These shield sleeves would have the same shape as the shield 15 shown in FIG. 9.

It is preferred if before use the carrier mat provided with mounting channels is fitted with the guide sleeves 2. This is advantageous because already existing guide sleeves 2 can be used. There is, however, the possibility that such guide sleeves 2 can be inserted already during the manufacture of the carrier mat, so that the mat is then available for the user practically fully fitted. Furthermore, the mounting channels 7 themselves can be constructed so that they themselves would form guides for the radiation source. In this case junctions are provided directly on tie carrier mat at the outlet ends of the mounting channels 7 to join them with the hollow probes 4 of the afterloading device 3. The shape of the carrier mat shown in the embodiments also simplifies the cutting of the carrier mat to suit, since grid-like separating lines are already present.

To enable the presentation of the carrier mat on the X-ray screen and thus control its position, X-ray opaque material inclusions 16 are provided in the mounting channels. In this embodiment each sphere 9 of the carrier mat 1 has such a material inclusion 16. To enable to distinguish the individual mounting channels of the carrier mat on the X-ray picture, the material inclusions may be positioned or constructed in the form of a code.

Figure 14:
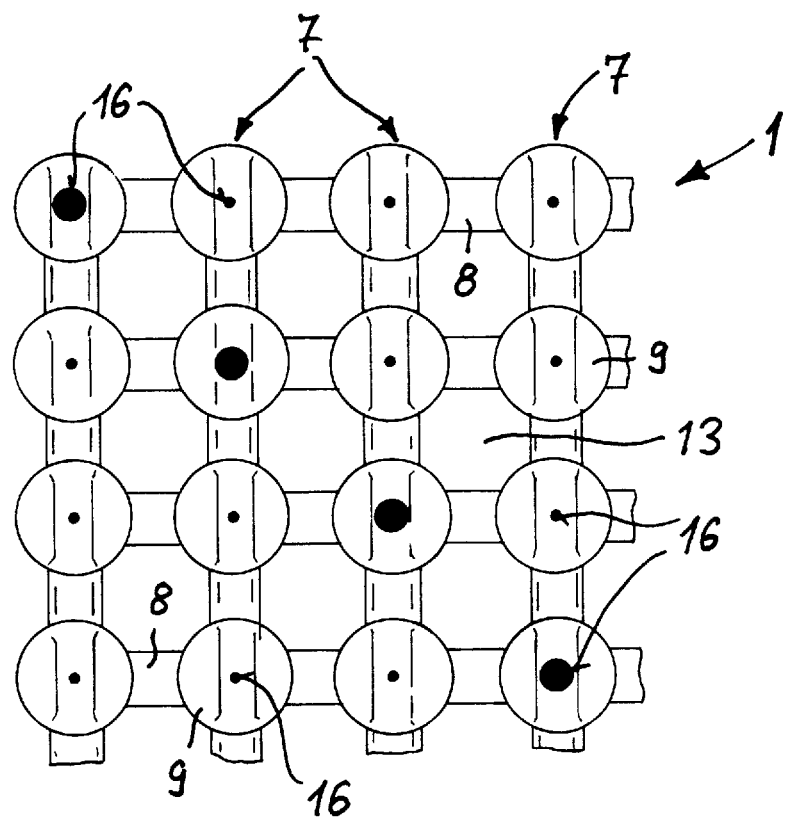

In the embodiment shown in FIG. 14 the coding is carried out in such a manner that in the first row in the first position, in the second row in the second position, etc. a slightly larger material inclusion is provided. However, the coding may be provided in a diversity of forms.

There is the further possibility that the carrier mat is provided with position sensors which are distributed preferably in a grid-shape and are connected to a computer. In this manner a direct illustration of the position of the carrier mat on the display unit is possible. With these position sensors a considerably more accurate dosage calculation can be carried out by taking into consideration the shape of the mat and the radiators guided in it. Due to this a considerably more accurate calculation of the dwell time of the radiator at the respective radiation places is also possible.

The mat can be also used for the treatment of external areas, for example, surface tumours. For this purpose it is placed on the area to be treated on the outside. There is the further possibility to introduce deformable stiffening elements into the mounting channels, which then will take care that the mat retains its shape once it has been adapted to a shape. By this it can be positioned always correctly in case of multiple use.

I claim:

1. A device for medical radiation therapy, comprising a deformable carrier mat (1, 1a) for application in a treatment area of a patient, in which mat an essentially point-shaped radiation source (5) is displaceable and positionable, the carrier mat (1, 1a) having prefabricated mounting channels (7, 7a, 7b, 7c) running within a plane of the mat to accommodate guide sleeves (2) for the radiation source, the carrier mat comprising a one-piece autoclavable material having a plurality of rounded shaped bodies (9, 9a) arranged next to each other and joined by collar sections (8), wherein the mounting channels run through at least one of the shaped bodies (9, 9a) and the collar sections (8).

2. The device according to claim 1, wherein the mounting channels are provided in a specifiable grid.

3. The device according to claim 2, wherein the mounting channels are provided substantially parallel to each other with an equal particular lateral distance from each other.

4. The device according to claim 1, wherein at least a portion of the mounting channels is provided offset relative to a central plane of the carrier mat running parallel to flat major surfaces of the carrier mat.

5. The device according to claim 4, wherein several mounting channels are provided above each other in different planes.

6. The device according to claim 1, wherein the mounting channels are provided at an angle to each other.

7. The device according claim 1, wherein the carrier mat has recesses (13) between the mounting channels (7) and between the shaped bodies (9, 9a).

8. The device according to claim 7, wherein the recesses are provided in a grid pattern distributed over the carrier mat.

9. The device according to claim 1, wherein the shaped bodies (9, 9a) are spaced from each other and the collar sections (8) comprise collar-shaped intermediate elements connecting the shaped bodies.

10. The device according to claim 1, wherein the shaped bodies (9, 9a) on sides which face each other in areas of joining by the collar sections (8) are flattened by half a length of the collar section and a distance between centers of adjacent shaped bodies corresponds to the shaped body diameter.

11. The device according to claim 1, wherein the mounting channels themselves comprise the sleeve guides for the radiation source.

12. The device according to claim 1, wherein the mounting channels themselves comprise hollow probes (4) connected to an afterloading device (3).

13. The device according to claim 1, wherein radiation shield elements (10, 10a, 15) are provided on a rear side of at least one of the carrier mat and the guide sleeves (2) in such a manner that an undesirable radiation at the rear side will be suppressed.

14. The device according to claim 13, wherein supports are provided on the shield elements to join them to the carrier mat, which supports have a form designed to engage recesses (13) in the carrier mat.

15. The device according to claim 14, wherein the supports are in a form of a mushroom.

16. The device according to claim 14, wherein the shield elements have a shape of a strip and extend at least over an extent of the shaped bodies (9, 9a).

17. The device according to claim 14, wherein the shield elements have a shape of a plate and extend over an extent of the shaped bodies (9, a) and the collar sections (8) adjoining them.

18. The device according to claim 14, wherein adjacent shield elements have engagement sections on their edges.

19. The device according to claim 14, wherein adjacent shield elements are provided overlapping in a manner similar to roof tiles.

20. The device according to claim 14, wherein the guide sleeves (2) have at least partial radiation shields (15), which overlap a section of a circumference of the guide sleeve.

21. The device according to claim 14, wherein as shield elements for the guide sleeves (2), longitudinally slotted shield sleeves are provided which are pushable onto the guide sleeves (2).

22. The device according to claim 1, wherein the guide sleeves (2) and the mounting channels (7) have longitudinal sections fitting the carrier mat which prevent rotation.

23. The device according to claim 1, wherein the mounting channels are provided with X-ray opaque material inclusions which are coded with regard to a position of each mounting channel.

24. The device according to claim 1, wherein the carrier mat is provided with manufacturer-installed guide sleeves (2).

25. The device according to claim 1, wherein the carrier mat is provided with position sensors, which sensors are connected to a computer with a display unit.

26. The device according to claim 25, wherein the position sensors are distributed in a grid pattern.

27. The device according to claim 1, wherein the autoclavable material comprises silicone.

28. The device according to claim 1, wherein the rounded shaped bodies are essentially spherical in form.

* * * * *